United States Patent [19]

Bams

[11] Patent Number: 6,125,293
[45] Date of Patent: Sep. 26, 2000

[54] METHOD FOR DETERMINING THE PH IN THE MUCOSA OF THE STOMACH OR THE GASTROINTESTINAL TRACT

[75] Inventor: Johannes Louis Bams, Peize, Netherlands

[73] Assignee: Academisch Ziekenhuis Groningen, Groningen, Netherlands

[21] Appl. No.: 09/225,656

[22] Filed: Jan. 5, 1999

Related U.S. Application Data

[63] Continuation of application No. PCT/NL97/00397, Jul. 8, 1997.

[30] Foreign Application Priority Data

Jul. 8, 1996 [NL] Netherlands ............................ 1003533

[51] Int. Cl.[7] ...................................................... A61B 5/00
[52] U.S. Cl. .......................... 600/361; 128/898; 600/345; 600/350
[58] Field of Search .................................... 600/300, 350, 600/345, 473, 573, 535, 364, 361, 397; 604/915; 128/207.15–207.14

[56] References Cited

U.S. PATENT DOCUMENTS

| | | | |
|---|---|---|---|
| 5,158,083 | 10/1992 | Sacristan et al. | 600/397 |
| 5,423,320 | 6/1995 | Salzman et al. | 600/473 |
| 5,456,251 | 10/1995 | Fiddian-Green | 600/345 |

FOREIGN PATENT DOCUMENTS

| | | |
|---|---|---|
| 0 089 647 A2 | 9/1983 | European Pat. Off. . |
| WO 90/01893 | 3/1990 | WIPO . |
| WO 94/21163 | 9/1994 | WIPO . |

*Primary Examiner*—Cary O'Connor
*Assistant Examiner*—Michael Astorino
*Attorney, Agent, or Firm*—Akin, Gump, Strauss, Hauer & Feld, L.L.P.

[57] ABSTRACT

The carbon dioxide tension in the wall of the stomach or gastrointestinal tract is determined by inserting into the stomach a semipermeable balloon filled with a saline solution. The result obtained from analyzing the carbon dioxide fraction in the saline solution is multiplied by a correction factor to obtain a stabilized measured value for the carbon dioxide fraction relating to the blood flowing through the wall of the stomach or the gastrointestinal tract, which stabilized measured value corresponds to a measured carbon dioxide fraction pertaining to a retention time of an hour or more, and multiplying the carbon dioxide tension $PaCO_2$ in the arterial blood with a first factor $F_1$ to obtain a first correction product, and multiplying the stabilized value of the carbon dioxide tension $PiCO_2$ in the blood flowing through the wall of the stomach or the gastrointestinal tract by a second factor $F_2$ to obtain a second correction product, and adding the first correction product to a basic factor $F_0$ and subtracting the second product therefrom in accordance with the formula:

$$pHi = F_0 + F_1 * PaCO_2 - F_2 * PiCO_2$$

in which pHi forms a measure for the pH of the stomach or the gastrointestinal tract.

3 Claims, No Drawings

METHOD FOR DETERMINING THE PH IN THE MUCOSA OF THE STOMACH OR THE GASTROINTESTINAL TRACT

CROSS-REFERENCE TO RELATED APPLICATION

This application is a continuation of International Application PCT/NL97/00397, filed Jul. 8, 1997, the disclosure of which is incorporated herein by reference.

BACKGROUND OF THE INVENTION

The invention relates to a method of determining the intramucosal pH of an animal or human stomach or gastrointestinal tract, comprising the determination of the carbon dioxide tension in the arterial blood and the determination of a carbon dioxide tension in the blood flowing through the wall of the stomach or gastrointestinal tract, by introducing into the stomach preferably a tube with a balloon which is permeable only for carbon dioxide and which is filled with a saline solution, and after a previously determined retention time of at least 30 minutes, removing said saline solution for analysis of the carbon dioxide fraction present in the saline solution.

Such a method is known from published International Patent Application WO 94/21163. By the known method the pH of, for instance, a stomach wall is determined by the assumption that the partial carbon dioxide pressure in the surface layers of the stomach wall is in equilibrium with those of the deeper layers of the stomach wall. A further assumption is that the bicarbonate concentration in the tissue is the same as the bicarbonate concentration in the arterial blood. The pH in the tissue is then determined by applying a modified version of the known "Henderson-Hasselbalch" equation, which reads:

$$pHa = 6.1 + \log[HCO_3] - \log[PaCO_2].$$

The terms pHa and $PaCO_2$ in this formula relate to the arterial blood. For the present objective the formula is modified by replacing $PaCO_2$ with $PiCO_2$ that is to say the carbon dioxide pressure in the stomach wall, and to assume as mentioned above, that the concentration of the bicarbonate in the tissue is in equilibrium with the bicarbonate concentration in the arterial blood. However, the problem is that this latter assumption is not correct, particularly with patients who are critically ill and are in septic or anaphylactic shock. As a result the pH measured according to the known method deviates from the actual pH, thus hindering a correct, and timely treatment of the patient.

In the known method, measurement of the partial carbon dioxide pressure in the stomach is obtained by inserting a silicone balloon containing a saline solution into the gastrointestinal tract whereby the carbon dioxide pressure in the saline solution should equilibrate with the carbon dioxide pressure in the gastrointestinal tract. Then the time required to achieve equilibration is measured and the partial carbon dioxide pressure in the saline solution is determined using a blood gas analyzer while, if necessary, a nomogram is used for the determination of the stabilized carbon dioxide value, departing from the stabilization time and the carbon dioxide pressure measured in the saline solution in combination with the bicarbonate concentration in a substantially simultaneously taken arterial blood sample.

To speed up the pH determination of the organ to be examined, WO 94/21163 suggests to compare the carbon dioxide pressure relating to the respective organ with the arterial bicarbonate concentration and/or another direct or indirect measurement of a global or systematic physiologic value, such as the pH, the carbon dioxide pressure or oxygen pressure of arterial, venous or other kind of blood, mixed venous bicarbonate, the carbon dioxide pressure in the exhalation air or other values and, in order to determine whether the condition of the respective organ renders it desirable that a) a bicarbonate concentration should be determined and/or b) what kind of clinical therapy or interference is necessary or desirable with regard to the oxygen supply to the respective organ.

BRIEF SUMMARY OF THE INVENTION

It is the object of the invention to provide a method as described in the preamble which affords a simple manner for a quick and reliable determination of the intramucosal pH of an animal or human stomach or gastrointestinal tract.

This is achieved with the method according to the invention by multiplying the result obtained from analyzing the carbon dioxide fraction in the saline solution with a correction factor to obtain a stabilized measured value for the carbon dioxide fraction relating to the blood flowing through the wall of the stomach or the gastrointestinal tract, which stabilized measured value corresponds to a measured carbon dioxide fraction pertaining to a retention time of an hour or more, and by multiplying the carbon dioxide tension $PaCO_2$ in the arterial blood with a first factor $F_1$ to obtain a first correction product, and the stabilized value of the carbon dioxide tension $PiCO_2$ in the blood flowing through the wall of the stomach or the gastrointestinal tract with a second factor $F_2$ to obtain a second correction product, and by adding the first correction product to a basic factor $F_0$ and subtracting the second correction product therefrom in accordance with the formula:

$$pHi = F_0 + F_1 * PaCO_2 - F_2 * PiCO_2,$$

in which pHi forms a measure for the pH of the stomach or the gastrointestinal tract.

At a retention time of 30 minutes said correction factor is 1.24. At another retention time the correction factor is different, for instance 1.17 at a retention time of 45 minutes.

DETAILED DESCRIPTION OF THE INVENTION

This new formula has proven to provide very reliable results. It has been shown that the most accurate measured values are obtained when the factors $F_0$, $F_1$, $F_2$ are adjusted to about 7.511, 0.0482 and 0.061 respectively. Clearly, the method according to the invention lends itself very effectively for the realization in a device for the automatic processing of arterial blood samples and saline solutions which, as described above, have been in the stomach of the respective patient for a previously chosen length of time.

Consequently, the application is also for exclusive rights for a device which is provided with means for carrying out the method according to the invention.

The invention will now be further elucidated by means of an example.

EXAMPLE

An experiment has been carried out for the validation of the method according to the invention and for the comparison of the results obtained thereby with regard to the results as they become available according to the prior art. To this end ten pigs weighing 30–40 kg each were anaesthetized with intramuscular ketamine in an amount of 15 mg/kg.

Sedation is maintained by means of isoflurane (1.3%–1.5%) and pancuronium. After intubation the animals are connected to a respirator and maintained at 100% $O_2$ in an amount of 15 ml/kg. The respiration rhythm is adjusted to maintain a partial carbon dioxide pressure of 40±5 Torr. The animals are kept on a core body temperature of 39±0.5° C. Blood samples were taken from a femoral artery. After the placement of several catheters an abdominal incision is made and a tube is inserted into the right carotid for bleeding the animal. A needle probe is placed in the stomach wall for measuring the direct pH value, and the abdominal incision is covered with blankets to prevent dehydration. The animals are then left in peace for 60 min. to stabilize. A tube is placed in the stomach for measuring the partial carbon dioxide tension. The needle probe used is calibrated with buffer solutions which calibration is repeated after each experiment in order to determine the stability of the probe.

The measuring protocol proceeded as follows:

1. After the operation the animals were left in peace for 60 min. to allow them to stabilize. After this period the first measurement was carried out, introducing into the stomach a balloon which is permeable only for carbon dioxide and which is filled with a saline solution, which solution is retained in the stomach for 30 minutes. In Table 1, the results from this first measurement are shown, indicated by $T_0$.
2. After the measurement mentioned under 1., the animals are bled dry to a systolic blood pressure of 50 mmHg. After the bleeding period, which lasted at the most 30 min., the next measurement is carried out. Said measurement being indicated in the Table by $T_1$.
3. The animals are then maintained for an hour in the shock condition associated with the activity carried out under 2., at the end of which a subsequent measurement took place; said measurement is indicated in the Table by $T_2$.
4. Subsequently, during a period of 30 min. the blood is retransfused and the another measurement is carried out, indicated in the Table by $T_3$.
5. After retransfusion the animals stabilize again for an hour and a final measurement is carried out indicated in the Table by $T_4$.

In all the above-mentioned measurements the retention time of the balloon in the stomach of the laboratory animals, which balloon is permeable only for carbon dioxide and which is filled with a saline solution, is set at 30 minutes. To obtain the stabilized measurement for the carbon dioxide fraction corresponding to the measured carbon dioxide fraction pertaining to a retention time in the stomach of an hour or more, a correction factor 1.24 is applied. In addition to the anaesthetic, each animal received 50 mg ranitidine to prevent acid production influencing the measurements. The results of the above-described experiment are shown in Table 1 below, in which the first figure always represents the mean value and the second figure the standard error of mean. In the first line of Table 1 the pH value of the mucosa as measured directly is given. The second line gives that same value as measured according to the prior art, applying the modified "Henderson-Hasselbalch" equation as described above. The third line, finally, gives the results as obtained by the method according to the invention.

TABLE 1

|  | $T_0$ | $T_1$ | $T_2$ | $T_3$ | $T_4$ |
|---|---|---|---|---|---|
| pHi-Direct | 7.271 ± 0.062 | 7.179 ± 0.052 | 7.149 ± 0.045 | 7.202 ± 0.051 | 7.241 ± 0.055 |
| pHi-"Old" | 7.259 ± 0.039 | 7.193 ± 0.029 | 7.189 ± 0.025 | 7.241 ± 0.028 | 7.284 ± 0.026 |
| pHi-"New" | 7.231 ± 0.056 | 7.178 ± 0.043 | 7.184 ± 0.034 | 7.244 ± 0.03 | 7.258 ± 0.032 |

Table 2 below gives the correlation analysis with respect to the results obtained.

TABLE 2

|  | $T_0$ | $T_1$ | $T_2$ | $T_3$ | $T_4$ |
|---|---|---|---|---|---|
| pHidir-pHi-"old" | 0.6831 | 0.8468 | 0.781 | 0.86 | 0.905 |
| pHidir-pHi-"New" | 0.76 | 0.977 | 0.866 | 0.93 | 0.947 |

These Tables show that the pH of the stomach wall determined by the method according to the invention correlates better with the directly measured pH than when said pH is determined by the method according to the prior art. In particular in the essential haemodynamic periods, represented by the measurements $T_1$(bleeding), $T_2$(shock phase) and $T_3$(retransfusion), the method according to the invention offers measuring results which correspond significantly better with the actual pH value than the pH values as determined according to the prior art.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

I claim:

1. A method of determining the intramucosal pH of an animal or human stomach or gastrointestinal tract, comprising determining a carbon dioxide tension in arterial blood and determining a carbon dioxide tension in blood flowing through a wall of the stomach or gastrointestinal tract by introducing into the stomach a tube with a balloon which is permeable only for carbon dioxide and which is filled with a saline solution, and after a previously determined retention time of at least 30 minutes, removing said saline solution for analysis of the carbon dioxide fraction present in the saline solution, and calculating from these two values of the carbon dioxide tension a value which serves as a gauge for the pH of the mucosa of the stomach or the gastrointestinal tract, multiplying the result obtained from analyzing the carbon dioxide fraction in the saline solution by a correction factor X, wherein the correction factor X is about 1.24, depending on said predetermined retention time to obtain a corrected value for the carbon dioxide fraction relating to the blood flowing through the wall of the stomach or the gastrointestinal tract, which corresponds to a measured carbon dioxide fraction pertaining to a retention time of an hour or more, and multiplying the carbon dioxide tension $PaCO_2$ in the arterial blood with a first factor $F_1$ to obtain a first correction product, and multiplying the corrected value of the carbon dioxide tension $PiCO_2$ in the blood flowing through the wall of the stomach or the gastrointestinal tract by a second factor $F_2$ to obtain a second correction product, and adding the first correction product to a basic factor $F_0$ and subtracting the second correction product therefrom in accordance with the formula:

$$pHi = F_0 + F_1 * PaCO_2 - F_2 * PiCO_2,$$

in which pHi forms a measure for the pH of the stomach or the gastrointestinal tract.

2. The method according to claim 1, wherein the factors $F_0$, $F_1$ and $F_2$ are adjusted to about 7.511, 0.0482 and 0.061 respectively.

3. The method according to claim 1, wherein the factors $F_0$, $F_1$ and $F_2$ are adjusted to about 7.511, 0.0482 and 0.061 respectively.

* * * * *